United States Patent
Gandon-Pain

(10) Patent No.: US 7,157,533 B2
(45) Date of Patent: Jan. 2, 2007

(54) PROCESS OF OBTAINING AN ISOPRENE-ENRICHED FCC C5 FRACTION AND SELECTIVE POLYMERIZATION OF ISOPRENE FROM SAID FRACTION

(75) Inventor: Sylvie Gandon-Pain, Clermont-Ferrand (FR)

(73) Assignee: Michelin Recherche et Technique S.A., Granges-Paccot (CH)

( * ) Notice: Subject to any disclaimer, the term of this patent is extended or adjusted under 35 U.S.C. 154(b) by 0 days.

(21) Appl. No.: 11/185,680

(22) Filed: Jul. 21, 2005

(65) Prior Publication Data

US 2006/0020095 A1    Jan. 26, 2006

Related U.S. Application Data

(63) Continuation of application No. PCT/EP2004/000343, filed on Jan. 19, 2004.

(30) Foreign Application Priority Data

Jan. 22, 2003   (FR) .................................. 03 00694

(51) Int. Cl.
*C08F 4/54* (2006.01)
*C07C 5/327* (2006.01)

(52) U.S. Cl. .................... 526/153; 526/75; 526/76; 526/164; 526/340.2; 585/252; 585/326; 585/523; 585/601; 585/810

(58) Field of Classification Search ............ 585/252, 585/326, 523, 601, 810; 526/75, 76, 153, 526/164, 340.2
See application file for complete search history.

(56) References Cited

U.S. PATENT DOCUMENTS 3,980,728 A * 9/1976 Khcheyan et al. ......... 585/500
5,753,583 A * 5/1998 Heineke et al. ............ 585/326

FOREIGN PATENT DOCUMENTS

FR        1.203.754 A    1/1960

WO        02/48218 A1    6/2002

OTHER PUBLICATIONS

English language translation of French Patent No. 1,203,754, publication date: Jan. 21, 1960.*

* cited by examiner

*Primary Examiner*—Fred Teskin
(74) *Attorney, Agent, or Firm*—Buchanan Ingersoll & Rooney PC

(57) ABSTRACT

A process is described for obtaining from an "FCC" initial C5 fraction which is enriched with isoprene and purified and usable for the selective polymerization of isoprene. A process is also described for obtaining an isoprene homopolymer from a polymerization medium comprising isoprene and at least one methyl butene, such as said "FCC" C5 fraction which is enriched with isoprene and purified. The process of obtaining the final fraction from the initial C5 fraction includes:

a catalytic hydrogenation reaction of said initial C5 fraction by a palladium-based catalyst, which produces an intermediate C5 fraction comprising n-pentenes in a mass ratio which is less than 0.1 % and methyl butenes, a dehydrogenation reaction applied to the intermediate C5 fraction, which includes methyl butenes to produce the final fraction, and purification of the final fraction to obtain a purified fraction which is practically devoid of disubstituted alkynes, true alkynes and cyclopentadiene, and the mass fraction of the methyl butenes in the intermediate fraction is <30 %. The process for obtaining an isoprene homopolymer includes the step of reacting, in the presence of isoprene and at least one methyl butene, a catalytic system based on a conjugated diene, a rare earth salt of an organic phosphoric acid in suspension, an alkylating agent, and a halogen donor, and the mass fraction of the methyl butenes in the intermediate fraction is <30 %. The process for obtaining an isoprene homopolymer includes the step of reacting, in the presence of isoprene and at least one methyl butene, a catalytic system based on a conjugated diene, a rare earth salt of an organic phosphoric acid in suspension, an alkylating agent, and a halogen donor.

23 Claims, No Drawings

PROCESS OF OBTAINING AN ISOPRENE-ENRICHED FCC C5 FRACTION AND SELECTIVE POLYMERIZATION OF ISOPRENE FROM SAID FRACTION

CROSS-REFERENCE TO RELATED APPLICATIONS

The present application is a continuation of PCT application No. PCT/EP2004/000343, filed Jan. 19, 2004, published in French on Aug. 5, 2004 as WO 2004/065339, which claims priority of French Application No. 0300694, filed Jan. 22, 2003, the contents of both applications being incorporated herein in their entirety.

BACKGROUND

1. Field of the Invention

The present invention relates to a process for obtaining, from a fluid catalytically cracked C5 fraction, a C5 fraction which is enriched with isoprene and purified which is usable to form a medium for the selective polymerization of isoprene. The invention also relates to a process for obtaining an isoprene homopolymer having in particular a high cis-1,4 linkage content and inherent viscosity, from a polymerization medium comprising isoprene and at least one methyl butene, such as said fluid catalytically cracked C5 fraction which is enriched with isoprene and purified.

2. Description of Related Art

Fluid catalytically cracked C5 fractions (also referred to as C5 fractions of fluid catalytically cracked light gasolines, or abbreviated to "F.C.C." fractions for "fluid catalytic cracking", in English) usually contain isoprene in a mass fraction of less than 1%. Furthermore, they contain essentially:

- in a mass fraction typically of between 40% and 65%, mono-olefins comprising, on one hand, α-olefins such as 1-butene, 3-methyl 1-butene, 1-pentene, 2-methyl 1-butene and, on the other hand, β-olefins such as 2-butene, 2-pentene and 2-methyl-2-butene;
- in a mass fraction typically of between 55% and 30%, alkanes comprising isopentane in a majority proportion and n-pentane in a minority proportion, and
- in a mass fraction typically of less than 1%, dienes such as cyclopentadiene, 1,3-pentadiene and 1,4-pentadiene, and other compounds such as acetylene compounds.

These fluid catalytically cracked C5 fractions must in particular not be confused with steam-cracked C5 naphtha fractions, which typically contain isoprene in a mass fraction ranging from 10% to 30%, mono-olefins (α-olefins and β-olefins) in a mass fraction ranging from 20% to 40%, dienes such as cyclopentadiene and pentadienes in a mass fraction ranging from 20% to 30%, and, in a minority proportion, alkanes, limonene and acetylenic and aromatic compounds.

In order to be able to effect selective polymerization of isoprene with high activity from such a steam-cracked C5 naphtha fraction, the latter must first be enriched with isoprene so that the mass fraction of isoprene in the enriched fraction is close to 100%, because it turns out that the other aforementioned compounds adversely affect the yield of the isoprene polymerization reaction. In particular, this enriched fraction must be practically devoid of cyclopentadiene, which is a poison to catalytic systems.

International patent specification WO-A-02/48218 in the name of the Applicants discloses a process for obtaining a polyisoprene having a very high cis-1,4 linkage content from such a steam-cracked C5 naphtha fraction enriched with isoprene, this process consisting essentially of reacting a catalytic system in the presence of the enriched C5 fraction such that the mass fraction of isoprene in the enriched fraction varies surprisingly from 30% to 95% only.

This catalytic system is based on a conjugated diene monomer, a rare earth salt of an organic phosphoric acid suspended in a saturated, inert hydrocarbon solvent, which is of aliphatic or alicyclic type, an alkylating agent consisting of an alkylaluminium of formula $AlR_3$ or $HAlR_2$, in which Al represents the aluminium atom, H represents a hydrogen atom and R represents a hydrocarbon radical, in a molar ratio (alkylating agent: rare earth salt) varying from 1 to 5, and a halogen donor consisting of an alkylaluminium halide.

In order to be able to effect selective polymerization of isoprene with high activity from a fluid catalytically cracked C5 fraction, this C5 fraction must also be enriched with isoprene so that the mass fraction of isoprene in the enriched fraction is close to 100%, typically greater than 99%, because it turns out that certain compounds of this enriched C5 fraction, such as the methyl butenes, adversely affect the yield of the isoprene polymerization reaction. Furthermore, the enriched fraction must be practically devoid of 1,3- and 1,4-pentadiene, which are known to impair the polymerization kinetics of the isoprene compared with that of isoprene taken in isolation.

In known manner, a mass fraction of isoprene of close to 100% in a fluid catalytically cracked C5 fraction may be obtained, in a first stage, by decomposition of amyl ether obtained by reaction of an alcohol with this C5 fraction in order to obtain a mass fraction of methyl butenes of close to 100% in the C5 fraction thus treated and purified, then, in a second stage, by oxidative dehydrogenation of the methyl butenes to isoprene. Reference will be made to patent specification FR-A-2 782 996 for the description of this enrichment of an "F.C.C." C5 fraction with isoprene.

One major disadvantage of the known processes of selective polymerization of isoprene from a fluid catalytically cracked C5 fraction lies in the necessity of considerably enriching this C5 fraction with isoprene via a complex enrichment process such as the one mentioned above with reference to document FR-A-2 782 996 and, consequently, of involving a relatively high overall operating cost for this polymerization.

SUMMARY OF THE INVENTION

The object of the present invention is to overcome this drawback, and it is achieved in that the Applicants have surprisingly discovered that a catalytic system based on:
- at least one conjugated diene monomer,
- a salt of one or more rare earth metals (metals having an atomic number of between 57 and 71 in the periodic table) of an organic phosphoric acid,
- an alkylating agent consisting of an alkylaluminium of formula $AlR_3$ or $HAlR_2$, in which Al represents the aluminium atom, H represents a hydrogen atom, the radicals R, which may be identical or different, and straight-chain or branched, represent hydrocarbon groups having from 1 to 8 carbon atoms, and
- a halogen donor consisting of an alkylaluminium halide, said salt being suspended in at least one saturated inert hydrocarbon solvent of aliphatic or alicyclic type which is included in said catalytic system, and the molar ratio (alkylating agent:rare earth salt) being in a range of from 1 to 5, permits the selective polymerization of isoprene with high catalytic activity to obtain a polyisoprene having a high cis-1,4 linkage content, from a fluid catalytically cracked initial C5 fraction which has been only slightly enriched with isoprene, such that the mass fraction of isoprene in the enriched and purified final C5 fraction is less than 30%, and advantageously less than or equal to 10%.

This possibility of homopolymerizing isoprene from this purified final C5 fraction, which is only very slightly enriched with isoprene, results in a simplification of the operation of enriching the initial C5 fraction and, consequently, a substantial reduction in the overall cost of obtaining polyisoprenes from said initial C5 fraction.

DETAILED DESCRIPTION OF THE INVENTION

According to another aspect of the present invention, a process for obtaining said final C5 fraction which is enriched with isoprene and purified which is usable to form a medium for the selective polymerization of isoprene in the presence of said catalytic system, from said fluid catalytically cracked initial C5 fraction, comprises:

dehydrogenation which is applied to an intermediate C5 fraction, comprising methyl butenes and resulting from said initial C5 fraction, and which produces said final C5 fraction, purification of said final C5 fraction thus obtained to obtain said purified final C5 fraction which is practically devoid of disubstituted alkynes, true alkynes (including vinylacetylenes) and cyclopentadiene, and this process for obtaining said purified final C5 fraction is such that the mass fraction of said methyl butenes in said intermediate C5 fraction is less than 30%.

Advantageously, the mass fraction of said methyl butenes in said intermediate C5 fraction is less than or equal to 20%.

It will be noted that this mass fraction of the methyl butenes in this intermediate C5 fraction (i.e. before dehydrogenation) is extremely reduced compared with the mass fractions of methyl butenes close to 100% which characterize the C5 fractions before dehydrogenation which are used in the known processes for enrichment with isoprene of the fluid catalytically cracked fractions, for the selective polymerization of isoprene with a high yield in order to obtain a polyisoprene having a high cis-1,4 linkage content.

According to another aspect of the present invention, said intermediate C5 fraction is depleted in n-pentenes such that it comprises said n-pentenes in a mass fraction of less than 0.1%.

It will be noted that this depletion in n-pentenes of the intermediate C5 fraction (precursors of the 1,3- and 1,4-pentadienes) makes it possible practically to eliminate these 1,3- and 1,4-pentadienes from the final C5 fraction.

In fact, according to another aspect of the invention, the final C5 fraction comprises 1,3-pentadiene and 1,4-pentadiene in mass ratios (1,3-pentadiene:isoprene) and (1,4-pentadiene:isoprene) which must be less than or equal to 0.5% and 0.2%, respectively, to be able to polymerize isoprene selectively from this final fraction with satisfactory conversion kinetics which are close to those relating to the isolated polymerization of isoprene (i.e. the polymerization medium comprising solely the solvent and isoprene) and to obtain a polyisoprene of high viscosity analogous to that of polyisoprene obtained in isolation.

According to another characteristic of the invention, said process for obtaining said final C5 fraction enriched with isoprene comprises a catalytic hydrogenation reaction, such as catalytic hydrogenation by means of a palladium-based catalyst, which is applied to said initial C5 fraction and which produces said intermediate C5 fraction.

According to another aspect of the present invention, the mass ratio (methyl butenes:isoprene) in said purified final C5 fraction is equal to or greater than 50%.

According to another aspect of the invention, the mass ratio (mono-olefins:isoprene) in said purified final C5 fraction may advantageously be greater than 50%.

For obtaining said purified final C5 fraction, the final C5 fraction is subjected to purification operations comprising:

distillation over maleic anhydride to remove practically any residual cyclopentadiene, elimination of the true alkynes and the disubstituted alkynes by distillation on diisobutylaluminium hydride (DiBAH), by a selective catalytic hydrogenation reaction or any other operation known to the person skilled in the art, and passing over alumina or over a molecular sieve to remove the residual polar impurities.

It will be noted that the final C5 fraction which is thus purified comprises in particular, as methyl butenes, 2-methyl 2-butene, and that it furthermore comprises minimal quantities:

of disubstituted alkynes, the mass ratio (disubstituted alkynes:isoprene) preferably being less than or equal to 0.7%, of true alkynes, the mass ratio (true alkynes:isoprene) in the purified final C5 fraction preferably being less than or equal to 15 ppm, of cyclopentadiene, the mass ratio (cyclopentadiene:isoprene) in this purified final C5 fraction preferably being less than or equal to 5 ppm.

The subject of the present invention is also a process for obtaining an isoprene homopolymer having a cis-1,4 linkage content equal to or greater than 98.0%, which is such that it comprises the reaction of said catalytic system according to the invention in a polymerization medium comprising isoprene and at least one methyl butene, such that the mass ratio (methyl butene(s):isoprene) is equal to or greater than 50% and advantageously equal to or greater than 100%.

It will be noted that this polymerization reaction can be implemented in an inert hydrocarbon solvent, or alternatively without a solvent.

According to another aspect of the invention relating to this process for obtaining an isoprene homopolymer, the polymerization medium comprises at least one mono-olefin and the mass ratio (mono-olefin(s):isoprene) is greater than 50% in this polymerization medium.

According to one preferred characteristic of this process for obtaining an isoprene homopolymer according to the invention, said methyl butenes comprise 2-methyl 2-butene.

Even more preferably, the mass ratio (2-methyl 2-butene:isoprene) in said polymerization medium is equal to or greater than 20% and, even more preferably, equal to or greater than 50%.

It will be noted that the fluid catalytically cracked C5 fractions and said purified final C5 fractions according to the present invention which result therefrom are characterized in that they always comprise 2-methyl 2-butene.

Even more preferably, said methyl butenes comprise at least 2-methyl 1-butene and 2-methyl 2-butene, the mass ratio (2-methyl 1-butene:isoprene) and the mass ratio (2-methyl 2-butene:isoprene) each being of between 20 and 60%.

According to another aspect of this process for obtaining an isoprene homopolymer according to the invention, the mass fraction of isoprene in said polymerization medium is less than 30% and advantageously less than or equal to 10%.

According to a preferred embodiment of this process for obtaining an isoprene homopolymer according to the invention, said process comprises the following stages:

(i) obtaining, from a fluid catalytically cracked initial C5 fraction, an intermediate C5 fraction comprising methyl butenes in a mass fraction of less than 30% and advantageously less than or equal to 20%, (ii) obtaining a final C5 fraction which is enriched with isoprene and purified, usable to form a medium for the selective polymerization of isoprene in the presence of said catalytic system, by dehydrogenation applied to said intermediate C5 fraction, and (iii) obtaining said isoprene homopolymer by reacting said enriched and purified final C5 fraction with said catalytic system.

According to another aspect of this preferred embodiment in which said polymerization medium is formed by said purified final C5 fraction, the mass ratio (mono-olefin(s): isoprene) is greater than 50% in this polymerization medium.

According to another characteristic of this preferred embodiment, said stage (i) comprises a catalytic hydrogenation, such as a catalytic hydrogenation by means of a palladium-based catalyst.

According to another aspect of this preferred embodiment, said intermediate C5 fraction is depleted in n-pentenes such that it comprises said n-pentenes in a mass fraction of less than 0.1%, and said final C5 fraction comprises 1,3-pentadiene and 1,4-pentadiene in mass ratios (1,3-pentadiene:isoprene) and (1,4-pentadiene:isoprene) which must be less than or equal to 0.5% and 0.2% respectively for the reasons given above.

According to another aspect of this preferred embodiment, said purified final C5 fraction comprises isoprene in a mass fraction of less than 30% and advantageously less than or equal to 10%.

According to another aspect of this preferred embodiment, the mass ratio (methyl butenes:isoprene) in said purified final C5 fraction is equal to or greater than 50%.

According to a preferred example of implementation of said process for obtaining an isoprene homopolymer, the polymerization reaction of the isoprene is performed at a temperature less than or equal to 5° C., so that said isoprene homopolymer has a cis-1,4 linkage content, measured according to the techniques of carbon 13 nuclear magnetic resonance or of mid-infrared analysis, which varies from 99.0% to 99.6%.

Reference will be made to patent specification W O-A-02/38635 in the name of the Applicants for a detailed description of the implementation of this reaction at a temperature less than or equal to 5° C.

Advantageously, polyisoprenes are obtained having cis-1,4 linkage contents, measured by one or the other of the aforementioned techniques, which are equal to or greater than 99.3% and belong even more advantageously to a range of from 99.3% to 99.6%, when the polymerization is effected at a temperature of from −55° C. to −20° C.

Even more advantageously, polyisoprenes are obtained which have cis-1,4 linkage contents, also measured by one or the other of the aforementioned techniques, which are equal to or greater than 99.5% and are for example equal to 99.6%, when the polymerization is effected at a temperature of from −55° C. to −45° C.

Generally, it will be noted that the particularly high cis-1,4 linkage content obtained for the polyisoprenes according to the invention is independent of the quantity of said catalytic system used.

According to another advantageous characteristic of the invention, the isoprene homopolymers which are obtained by said process have inherent viscosities, measured at 0.1 g/dl in toluene at 25° C., which are greater than 3 dl/g, advantageously greater than 4 dl/g.

It will be noted that the catalytic system according to the invention has the advantage of imparting, to the polymerization reaction for the isoprene, practically one and the same advantageous conversion kinetics for the isoprene and, to the polyisoprenes obtained, practically the same high values of inherent viscosity at given conversion rates, whether or not the polymerization medium comprises said methyl butenes.

According to one preferred characteristic of said catalytic system according to the invention, the molar ratio (alkylating agent:rare earth salt) is in a range from 1 to 2.

According to another preferred characteristic of said catalytic system according to the invention, said rare earth salt is a rare-earth tris[bis(2-ethylhexyl)phosphate], such as neodymium tris[bis(2-ethylhexyl)phosphate].

According to another preferred characteristic of the invention, said catalytic system satisfies at least one of the following conditions:

(a) said catalytic system comprises said rare earth metal(s) in a concentration which lies within a range of from 0.01 to 0.06 mol/l, (b) the molar ratio (halogen donor:rare earth salt) varies from 2.0 to 3.5, (c) the molar ratio (conjugated diene monomer: rare earth salt) varies from 15 to 70, (d) said conjugated diene monomer is butadiene, (e) said alkylating agent is diisobutylaluminium hydride, and (f) said halogen donor is diethylaluminium chloride.

1,3-butadiene may be mentioned as a preferred conjugated diene monomer usable for "preforming" the catalytic system according to the invention.

Mention may also be made of 2-methyl-1,3-butadiene (or isoprene), 2,3-di(C1 to C5 alkyl)-1,3-butadienes such as, for example, 2,3-dimethyl-1,3-butadiene, 2,3-diethyl-1,3-butadiene, 2-methyl-3-ethyl-1,3-butadiene, 2-methyl-3-isopropyl-1,3-butadiene, phenyl-1,3-butadiene, 1,3-pentadiene, 2,4-hexadiene, or any other conjugated diene having between 4 and 8 carbon atoms.

According to another characteristic of the invention, said rare earth salt consists of a non-hygroscopic powder having a slight tendency to agglomerate at ambient temperature.

According to a preferred embodiment of the invention, the inert hydrocarbon solvent in which said rare earth salt is suspended is a low molecular weight aliphatic or alicyclic solvent, such as cyclohexane, methylcyclohexane, n-heptane or a mixture of these solvents.

According to another embodiment of the invention, the solvent used to suspend the rare earth salt is a mixture of a high molecular weight aliphatic solvent comprising a paraffinic oil, for example petrolatum oil, and of a low molecular weight solvent such as those mentioned above (for example methylcyclohexane).

This suspension is prepared by dispersive grinding of the rare earth salt in this paraffinic oil in such a manner as to obtain a very fine, homogeneous suspension of the salt.

As indicated above, said catalytic system comprises the rare earth metal in a concentration which lies within a range of from 0.01 to 0.06 mol/l, for example equal to or substantially equal to 0.02 mol/l.

Alkylating agents of the formula $AlR_3$ or $HAlR_2$ usable in the catalytic system according to the invention which may be mentioned are alkylaluminiums such as:

trialkylaluminiums, for example triisobutylaluminium, or dialkylaluminium hydrides, for example diisobutylaluminium hydride.

It will be noted that this alkylating agent is preferably formed of diisobutylaluminium hydride (referred to as DiBAH in the rest of the present description).

Halogen donors usable in the catalytic system according to the invention which may be mentioned are alkylaluminium halides, preferably diethylaluminium chloride (referred to as DEAC in the rest of the present description).

As indicated above, the molar ratio (halogen donor:rare earth salt) may have a value ranging from 2.0 to 3.5.

According to the invention, the process for the preparation of said catalytic system consists:
in a first stage, of preparing a suspension of said salt in said solvent,
in a second stage, of adding said conjugated diene monomer to the suspension,
in a third stage, of adding said alkylating agent to the suspension comprising said monomer to obtain an alkylated salt, and
in a fourth stage, of adding said halogen donor to the alkylated salt.

The aforementioned characteristics of the present invention, as well as others, will be better understood on reading the following description of several examples of embodiment of the invention, which are given by way of illustration and not of limitation.

I. Preparation of a Catalytic System According to the Invention:

1) Synthesis of an Organic Neodymium Phosphate Salt According to the Invention:

a) Synthesis of an Aqueous Solution of Neodymium $NdCl_3, 6H_2O$

A given quantity of $Nd_2O_3$ was introduced into a reactor. 31.25 kg of demineralised water was added per kg of $Nd_2O_3$. 1.56 l of 36% by weight concentrated HCl (d=1.18) is added slowly, at ambient temperature, per kg of $Nd_2O_3$.

The reaction $Nd_2O_3 + 6\ HCl + 9H_2O \rightarrow 2\ NdCl_3, 6H_2O$ is highly exothermic.

Once all the hydrochloric acid has been added, the solution is brought to boiling with stirring for 30 minutes, in order to eliminate the excess HCl. The aqueous $NdCl_3$ solution is clear and mauve in colour. No insoluble product ($Nd_2O_3$) remains.

The pH of the solution, measured at 25° C., is corrected by adding 2 moles per liter sodium hydroxide. The final pH is approximately 4.5.

b) Synthesis of an Organic Sodium Phosphate of Formula $[RO]_2P(O)ONa$ (R=2-ethylhexyl 27.8 kg of demineralised water per kg of $Nd_2O_3$ from the synthesis of section a) above is introduced into an empty reactor. 0.708 kg of NaOH pellets are dissolved per kg of $Nd_2O_3$ of said section a). 10.4 l acetone and 5.819 kg of an organic phosphoric acid (bis(2ethylhexyl) phosphoric acid, listed in the "Aldrich" catalogue under the reference 23.782–5), were added to another reactor, still per kg of initial $Nd_2O_3$.

At ambient temperature, the solution of said organic phosphoric acid is poured into the solution of NaOH. The reaction is as follows:

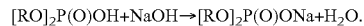

This reaction is slightly exothermic, and a clear-coloured homogeneous solution is obtained. The pH of the solution, measured at 25° C., is equal to 5.4.

c) Synthesis of a Phosphated Neodymium Salt of the Formula $[[RO]_2P(O)O]_3Nd$

The aqueous solution of $NdCl_3, 6H_2O$ obtained in section a) above is poured on to the organic Na phosphate solution obtained in section b) above, with vigorous stirring and at a temperature of 45° C. Depending on the case, the addition may be performed in the reverse order. A very fine white precipitate forms immediately. The mixture obtained is kept stirred for 15 minutes, after the addition of all the organic Na phosphate:

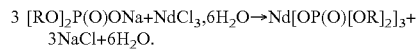

The resultant phosphated neodymium salt is recovered by sedimentation and washed with a mixture of 45 liters of demineralised water and 15 liters of acetone for 15 minutes. The phosphated neodymium salt is then recovered by centrifugation.

The pH of the mother liquors is between 2 and 3 at 25° C. These mother liquors are colourless and clear. The qualitative analytic test for chlorides is virtually negative for the final washing water (the reaction is as follows: $NaCl + AgNO_3$ ($HNO_3$ medium) $\rightarrow AgCl \downarrow + NaNO_3$).

The neodymium salt washed in this manner is dried in an oven at 60° C., under a vacuum and with air-flow for 72 hours.

2) Synthesis of a "preformed" Catalytic System According to the Invention:

a) Composition of the Catalytic System

The catalytic system comprises a phosphated neodymium salt as synthesized in section 1) above, which is suspended in a low molecular weight inert hydrocarbon solvent (consisting of methylcyclohexane, abbreviated to "MCH" hereafter).

The catalytic system is characterized by the following relative molar ratios, with respect to the neodymium salt:

Nd salt: butadiene (Bd): DiBAH: DEAC=1:30:1.8:2.6.

The final concentration of Nd in the catalytic system is 0.02 M.

b) Process for Synthesizing the Catalytic System

First Stage:

In order to obtain the catalytic system, 550 g of neodymium salt, in powdered state, is poured into a reactor which has been cleaned of its impurities beforehand. This salt is then subjected to nitrogen bubbling from the bottom of the reactor for a period of 15 minutes.

Second Stage:

Approximately 90% (mass fraction) of the solvent mentioned in section 2)a) above is introduced into the reactor containing the neodymium salt, the duration of the contacting of the neodymium salt with this solvent being 30 min, the temperature of contact being 30° C.

Third Stage:

Then butadiene is introduced into the reactor (in the molar ratio salt:butadiene of 1:30 mentioned in section 2)a) above) at a temperature of 30° C., in order to "preform" the catalytic system.

Fourth Stage:

Then DiBAH as alkylating agent for the neodymium salt is introduced into the reactor, in a concentration of approximately 1 M in the MCH. The duration of the alkylation is 30 min. and the temperature of the alkylation reaction is 30° C.

Fifth Stage:

Then DEAC as halogen donor is introduced into the reactor, in a concentration of approximately 1 M in the MCH. The temperature of the reaction medium is adjusted to 60° C.

Sixth Stage:

"Preforming" (or ageing) of the mixture thus obtained is then carried out by maintaining this temperature of 60° C. for a period of 2 hours.

Seventh Stage:

There is thus obtained a solution of catalytic system. The reactor is emptied and this solution is transferred to a 750 ml "Steinie" bottle, which has beforehand been washed, dried and subjected to nitrogen bubbling.

Finally, the catalytic solution is stored under a nitrogen atmosphere in a freezer at a temperature of −15° C.

Table 1 hereafter contains the characteristics of the catalytic system and its preparation process.

TABLE 1

|  | Catalytic system |
|---|---|
| Nd:Bd:DiBAH:DEAC | 1:30:1.8:2.6 |
| Solvation | MCH |
| (solvent/duration/temperature) | 30 min. |
|  | 30° C. |
| Volume MCH (liters) | 20.5 |
| Weight Nd phosphate (g) | 550 |
| Weight of butadiene (g) | 804 |
| Alkylation | 30 min. |
| (duration, temperature) | 30° C. |
| Volume of DiBAH (ml) | 1007 |
| Strength of DiBAH (mol/l) | 0.89 |
| Ageing of DEAC | 2 hours |
| (duration, temperature) | 60° C. |
| Volume of DEAC (ml) | 1310 |
| Strength of DEAC (mol/l) | 0.985 |

II. "Control" Test and Test According to the Invention for Polymerization of Isoprene by Means of the Catalytic System Prepared in § I:

The polymerization reactor is a 250 ml "Steinie" bottle, which contains 10.2 g isoprene and the tightness of which is ensured by a "septum/open-top seal" assembly which permits addition of said catalytic system according to the invention using a syringe.

The polymerization of the isoprene is carried out in cyclohexane at 50° C. in an inert nitrogen atmosphere (the cyclohexane having been subjected to nitrogen bubbling for 10 minutes beforehand).

The "control" test and the test according to the invention were carried out using 2.3 ml of said catalytic system, or a quantity of neodymium catalytic base of 450 micromoles per 100 grams of isoprene monomer (abbreviated to µMcm).

Furthermore, the same mass ratio S:M (solvent:isoprene monomer) which is equal to 9 and the same mass fraction of isoprene in the polymerization medium which is equal to 10% were used for these tests.

Acetylacetone was used as a shortstopping agent for each polymerization reaction (1 ml of an acetylacetone solution of a concentration of 1M in cyclohexane), and N-1,3-dimethylbutyl-N'-phenyl-p-phenylenediamine (abbreviated to 6PPD) as a protection agent (in a concentration of 0.4 phr).

Then each extracted solution was dried for approximately 18 hours in an oven at 60° C. under a vacuum (at a pressure of 200 mm Hg), under a gentle stream of nitrogen.

The conversion rate of isoprene to polyisoprene as a function of reaction time is measured to describe the polymerization kinetics for each "control" test and each test according to the invention.

The inherent viscosity at 0.1 g/dl in toluene, measured at 25° C., characterizes the macrostructure of each polyisoprene obtained.

1) "Control" Polymerization Test in the Absence of Methyl Butene:

In this "control" test practically pure isoprene which had been extracted conventionally in a laboratory from a steam-cracked C5 naphtha fraction was used, by effecting:

distillation of the initial C5 fraction over maleic anhydride to remove any residual cyclopentadiene, followed by passage through an alumina column to remove polar impurities, and nitrogen bubbling for 10 min., immediately prior to the polymerization reaction.

The mass fraction of isoprene extracted from this C5 fraction was determined, by gas phase chromatography (GPC, see Appendix 3), and is 99.2%.

For this "control" test, 15 ml isoprene (or 10.2 g) and 128 ml cyclohexane as polymerization solvent were used, such that the mass fraction of isoprene in the polymerization medium is substantially equal to 10%.

Table 2 hereafter shows the results obtained for this "control" test.

TABLE 2

| Polymerization time (min.) | Conversion rate (%) | Inherent viscosity (dl/g) |
|---|---|---|
| 10 | 32 | — |
| 20 | 68 | — |
| 30 | 86 | — |
| 60 | 104 | 4.26 |

2) Polymerization Test According to the Invention in the Presence of Methyl Butenes:

In this test according to the invention a polymerization medium comprising approximately 10% isoprene, 5% 2-methyl 1-butene, 5% 2-methyl 2-butene and 80% cyclohexane (mass fractions) was used.

In this test 15 ml (or 10.2 g) of the isoprene prepared in § II. 1) above (approximately 99.2% pure) and 113 ml cyclohexane was used.

The 2-methyl 1-butene used is obtained by purification, carried out by means of passing drop by drop over an alumina column a 2-methyl 1-butene which is approximately 95% pure, sold by Fluka. 7.8 ml of 2-methyl 1-butene, or 5.1 g, was used.

The 2-methyl 2-butene used is obtained by purification, carried out by means of passing drop by drop over an alumina column a 2-methyl 2-butene which is approximately 85% pure, sold by Fluka (this 2-methyl 2-butene was analysed by gas phase chromatography as being 93% pure). 7.7 ml of 2-methyl 2-butene, or also 5.1 g, was used.

Table 3 hereafter shows the results obtained for this test according to the invention.

TABLE 3

| Polymerization time (min.) | Conversion rate (%) | Inherent viscosity (dl/g) |
|---|---|---|
| 10 | 25 | — |
| 20 | 57 | — |
| 30 | 77 | — |
| 60 | 101 | 4.42 |

3) Conclusions:

Tables 2 and 3 show that the catalytic system according to the invention, based on a conjugated diene monomer, a rare earth salt of an organic phosphoric acid suspended in an inert, saturated hydrocarbon solvent, an alkylating agent consisting of an alkylaluminium of formula $AlR_3$ or $HAlR_2$ with a molar ratio (alkylating agent:salt) of from 1 to 5, and a halogen donor consisting of an alkylaluminium halide, makes it possible to polymerize isoprene selectively in the presence of 2-methyl 1-butene and 2-methyl 2-butene with a mass ratio (methyl butenes:isoprene) equal to 100% (the mass ratios (2-methyl 1-butene:isoprene) and (2-methyl 2-butene:isoprene) each being 50%), for obtaining a polyisoprene having a cis-1,4 linkage content equal to or greater than 98.0% and an inherent viscosity greater than 4.0 dl/g.

It will be noted that the kinetics of conversion of the isoprene into polyisoprene relative to the test according to the invention in the presence of methyl butenes is very close to the kinetics relative to the "control" test without methyl butene. Furthermore, the inherent viscosity of the polyisoprene obtained in the test according to the invention is very close to that of the polyisoprene obtained in this "control" test.

III. Obtaining of Final Fractions Enriched with Isoprene Whether or Not in Accordance with the Invention, from Fluid Catalytically Cracked Initial Fractions, for the Selective Polymerization of Isoprene in the Presence of the Catalytic System of § I.:

1) Examples of Hydrogenation of Initial Fractions A and B for Obtaining Intermediate Fractions Whether or Not in Accordance with the Invention, at Various Hydrogenation Rates:

In this first hydrogenation stage, a crude initial fluid catalytically cracked C5 fraction A or B (see composition in Table 4 hereafter) was subjected to a hydrogenation reaction, which was performed in the following manner according to one example of embodiment of the invention.

1 g of catalyst based on palladium and calcium carbonate (of formula $Pd/CaCO_3$ and containing 5% by weight of Pd) and 100 ml of the initial C5 fraction are introduced into a 750 ml bottle. The bottle being capped at an initial pressure of 4 bar hydrogen and being agitated at 25° C., the hydrogen pressure is adjusted to 4 bar every hour for 3 hours. The total reaction time is 6 hours and 30 minutes.

The effect of this hydrogenation reaction is in particular to hydrogenate the n-pentenes contained in the initial fraction at a given hydrogenation rate T, so as to reduce the quantity of n-pentenes in the intermediate hydrogenated fraction for the second dehydrogenation stage, the effect of which is to transform these n-pentenes into 1,3- and 1,4-pentadienes.

a) Initial Fraction A and Intermediate Fraction A1 According to the Invention, Hydrogenated at a Rate T1

Table 4 hereafter shows the composition of said initial C5 fraction A and the intermediate C5 fraction A1 obtained following the above example of hydrogenation reaction at a hydrogenation rate T1 (the compositions are expressed in mass fractions in the corresponding fraction in % or in ppm, with 1 ppm=1 part per million=$10^{-4}$%).

TABLE 4

|  | Initial C5 fraction A | Intermediate C5 fraction A1 (hydrogenation at a rate T1) |
|---|---|---|
| Isoprene | 0.27% | not determined |
| Isopentane | 41.62% | 46.83% |
| Pentane | 4.54% | 24.92% |
| Propene | not determined | not determined |
| 1-butene | 0.04% | <100 ppm |
| 2-butene (E) | 0.18% | <10 ppm |
| 2-butene (Z) | 0.26% | <10 ppm |
| 2-pentene (E) | 9.69% | 750 ppm |
| 2-pentene (Z) | 5.19% | 143 ppm |
| 1-Pentene | 4.26% | 70 ppm |
| 2-methyl 1-butene | 11.21% | 1.28% |
| 3-methyl 1-butene | 1.69% | 105 ppm |
| 2-methyl 2-butene | 16.39% | 21.51% |
| 1,4-pentadiene | 92 ppm | <10 ppm |
| 1,3-pentadiene (E + Z) | 0.30% | 40 ppm |
| Cyclopentadiene | 0.15% | not determined |
| Total methyl butenes | 29.29% | 22.79% |
| Total n-pentenes | 19.14% | 963 ppm |

It will be noted that the intermediate fraction A1 obtained, which is intended to be subjected to the dehydrogenation reaction to enrich it with isoprene, comprises a mass fraction of methyl butenes (less than 30%) which is very much less than the mass fraction close to 100% which is usually required for the dehydrogenation, in order to obtain a final fraction usable for the homopolymerization of isoprene.

It will also be noted that the hydrogenation has made it possible to deplete the initial fraction A in n-pentene before dehydrogenation such that the intermediate fraction A1 comprises less than 0.1% of n-pentenes, whereas said initial fraction A contained close to 20% thereof.

b) Initial Fraction B and Intermediate Fractions B2 to B6 Whether or not in Accordance with the Invention:

Another initial C5 fraction B similar to the initial C5 fraction A above was subjected to hydrogenation reactions carried out analogously and characterized by other hydrogenation rates of the n-pentenes T2 to T5, as illustrated in Table 5 hereafter.

TABLE 5

|  | Initial fraction B | Intermed. fraction B2: rate T2 | Intermed. fraction B3: rate T3 | Intermed. fraction B4: rate T4 | Intermed. fraction B5: rate T5 | Intermed. fraction B6: rate T6 |
|---|---|---|---|---|---|---|
| 1-pentene | 4.20% | 0.06% | 0.02% | 80 ppm | 90 ppm | ≈59 ppm |
| 2-pentene (E + Z) | 15.10% | 4.40% | 0.80% | 0.34% | 0.30% | ≈9 ppm |

TABLE 5-continued

|  | Initial fraction B | Intermed. fraction B2: rate T2 | Intermed. fraction B3: rate T3 | Intermed. fraction B4: rate T4 | Intermed. fraction B5: rate T5 | Intermed. fraction B6: rate T6 |
|---|---|---|---|---|---|---|
| 2-methyl 1-butene | 11.20% | 1.70% | 1.50% | 1.10% | 1.10% | 0.70% |
| 3-methyl 1-butene | 1.60% | 0.01% | 0.01% | 50 ppm | 70 ppm | 38 ppm |
| 2-methyl 2-butene | 16.70% | 24.60% | 23.10% | 22.70% | 22.50% | 17.70% |
| isopentane | 41.10% | 44.20% | 45.40% | 46.30% | 46.90% | 51.60% |
| pentane | 4.60% | 20.00% | 23.60% | 24.30% | 24.10% | 24.70% |
| Total methyl butenes | 29.50% | 26.31% | 24.61% | 23.81% | 23.61% | 18.40% |
| Total of n-pentenes | 19.30% | 4.46% | 0.82% | 0.35% | 0.31% | ≈68 ppm |

It will be noted that each of the intermediate fractions B2 to B6 obtained, which are intended to be subjected to dehydrogenation in order to enrich them with isoprene, comprises a mass fraction of methyl butenes (less than 30%, or even less than 20% for fraction B 6) which is very much lower than the mass fraction of close to 100% which is usually required before dehydrogenation, in order to obtain a final fraction usable for homopolymerization of isoprene.

It will also be noted that the hydrogenation at the rates T2 to T5 did not make it possible to deplete the initial fraction B in n-pentenes before dehydrogenation such that each intermediate fraction comprises less than 0.1% of n-pentenes. Consequently, the intermediate fractions B2 to B5 cannot be used to obtain final fractions according to the invention comprising at most 0.5% of 1,3-pentadiene and at most 0.2% of 1,4-pentadiene, which is a necessary condition to be able to polymerize selectively isoprene with satisfactory conversion kinetics close to those relating to the isolated polymerization of isoprene and to obtain a polyisoprene of a viscosity analogous to that of polyisoprene obtained in isolation.

On the other hand, the hydrogenation of the initial fraction B at the rate T6 made it possible to deplete this in n-pentenes before dehydrogenation, such that the intermediate fraction B6 thus obtained comprises less than 0.1% of n-pentenes and is therefore in accordance with the invention.

2) Examples of Dehydrogenation of the Intermediate Fractions A1, B5 and B6:

Of the hydrogenated intermediate fractions A1 and B2 to B6, the intermediate fractions A1, B5 and B6 were subjected to dehydrogenation operations for example implemented as follows.

a) Dehydrogenation of the Intermediate Fraction A1 in Order to Obtain the Final Fraction A1' According to the Invention This intermediate fraction A1 is introduced into a reactor containing a 140 ml catalytic bed heated to a temperature of between 600° C. and 700° C., under currents of steam and nitrogen preheated to 650° C.

The flow rates of the intermediate fraction A1, the steam and the nitrogen are 1.63 mL/min., 1460 mL/min. and 3.76 ml/min respectively.

The catalytic bed is formed of iron oxide, chromium and potassium carbonate, and is sold by SHELL under the name "Shell 105".

On emerging from the reactor and after condensation of the majority of the water, the effluents come into contact with a calcium chloride "trap" and an alumina "trap", before being condensed in a bath of dry ice and acetone (at approximately –60° C.).

Table 6 hereafter shows the composition of the final fraction A1' thus obtained.

TABLE 6

|  | Initial fraction A | Intermediate fraction A1 | Final fraction A1' |
|---|---|---|---|
| Isoprene | 0.27% | Not determined | 11.00% |
| Isopentane | 41.62% | 46.83% | 48.80% |
| Pentane | 4.54% | 24.92% | 25.40% |
| Propene | not determined | Not determined | 0.38% |
| 1-butene | 0.04% | <100 ppm | 1.48% |
| 2-butene (E) | 0.18% | <10 ppm | 0.18% |
| 2-butene (Z) | 0.26% | <10 ppm | 0.14% |
| 2-pentene (E) | 9.69% | 750 ppm | 220 ppm |
| 2-pentene (Z) | 5.19% | 143 ppm | 130 ppm |
| 1-pentene | 4.26% | 70 ppm | 147 ppm |
| 2-methyl 1-butene | 11.21% | 1.28% | 2.53% |
| 3-methyl 1-butene | 1.69% | 105 ppm | 0.54% |
| 2-methyl 2-butene | 16.39% | 21.51% | 4.10% |
| 1,4-pentadiene | 92 ppm | <10 ppm | <50 ppm |
| 1,3-pentadiene (E + Z) | 0.30% | 40 ppm | 530 ppm |
| Cyclopentadiene | 0.15% | Not determined | 90 ppm |
| Total methyl butenes | 29.29% | 22.79% | 7.17% |
| Total n-pentenes | 19.14% | 963 ppm | 497 ppm |
| Total α-olefins | 17.20% | 1.28% | 4.93% |
| Total β-olefins | 31.71% | 21.51% | 4.42% |
| Total mono-olefins | 48.91% | 22.79% | 9.35% |

It will be noted that the final fraction A1' is in particular characterized in that it comprises:
- isoprene in a mass fraction practically equal to 10%,
- methyl butenes in a mass ratio (methyl butenes: isoprene) of 65%,
- mono-olefins in a mass ratio (mono-olefins: isoprene) of 85%.

It will also be noted that the hydrogenation stage, by the significant reduction in the amount of n-pentenes which it brings about, makes it possible to minimise the amount of pentadienes in the final fraction A'1, because the mass ratios (1,3-pentadiene:isoprene) and (1,4-pentadiene:isoprene) are respectively less than 0.5% and 0.2% in the final fraction A'1, which makes it usable after purification (intended to eliminate the disubstituted alkynes, the true alkynes and the cyclopentadiene) for the selective polymerization of isoprene.

3) Polymerization of the Isoprene Contained in the Final Fraction A'1 by means of the Catalytic System "preformed" According to the Invention:

a) Purification of the Final Fraction A'1 before Polymerization 1100 ml of the final fraction A' 1 before purification is used which is subjected in a first stage to distillation on maleic anhydride under the following conditions:

distillation column: 20 theoretical plates
reflux ratio: 5
maleic anhydride:cyclopentadiene: 30 (molar ratio), or 3 g of maleic anhydride
contacting of the maleic anhydride and the fraction: one night at ambient temperature and in a second stage to elution in an alumina column containing 250–300 cm³ of regenerated alumina, kept under nitrogen, with two successive passes, slowly drop by drop (100 ml/h).

b) Polymerization of the Isoprene Contained in this Purified Final Fraction A'1

The final fraction A'1 containing 3.42 g isoprene is polymerized using the "preformed" catalytic system according to the invention, described in § I-2)a), by operating in accordance with the process and the conditions described in § II, except for the fact that a quantity of neodymium catalytic base of 1170 micromoles is used per 100 grams of isoprene monomer and that the polymerization is effected for 220 minutes.

Table 7 hereafter shows the results obtained for this test according to the invention.

TABLE 7

| Polymerization time (min) | Conversion rate (%) | Inherent viscosity (dl/g) |
|---|---|---|
| 15 | 25 | |
| 30 | 40 | |
| 50 | 56 | |
| 80 | 72 | |
| 120 | 83 | |
| 220 | 97 | 4.86 |

The amount of cis measured by 13 carbon NMR analysis of the polyisoprene is 98.1%

Polydispersity index measured by SEC: 2.6 c) Dehydrogenation of the Intermediate Fraction B5 in Order to Obtain Three Final Fractions B5', B5" and B5'" not in Accordance with the Invention:

Table 8 below shows the compositions of three final fractions B5', B5", B5'" obtained respectively by dehydrogenation operations applied to the aforementioned intermediate fraction B5 according to § III. 2) a) above, at three temperatures of 625° C., 650° C. and 675° C.

TABLE 8

| | Initial fraction B | Intermediate fraction B5: hydrogenation at a rate T5 | Final fraction B5': dehydrogen. at 625° C. | Final fraction B5": dehydrogen. at 650° C. | Final fraction B5'": dehydrogen. at 675° C. |
|---|---|---|---|---|---|
| isoprene | | not determined | 13.00% | 12.60% | 12.60% |
| 1-pentene | 4.20% | 90 ppm | 0.04% | 0.02% | 0.03% |
| 2-pentene (E + Z) | 15.10% | 0.30% | 0.11% | 0.08% | 0.08% |
| 1,4-pentadiene:isoprene | | | 0.06% | 0.06% | 0.06% |
| 1,3-pentadiene:isoprene | | | 1.40% | 1.20% | 0.90% |
| 2-methyl 1-butene | 11.20% | 1.10% | 2.80% | 2.30% | 1.80% |
| 3-methyl 1-butene | 1.60% | 70 ppm | 0.50% | 0.50% | 0.30% |
| 2-methyl 2-butene | 16.70% | 22.50% | 4.70% | 3.70% | 2.80% |
| isopentane | 41.10% | 46.90% | 44.60% | 44.80% | 44.70% |
| Pentane | 4.60% | 24.10% | 25.80% | 24.40% | 24.90% |
| Total methyl butenes | 29.50% | 23.61% | 8.00% | 6.50% | 4.90% |
| Total n-pentenes | 19.30% | 0.31% | 0.15% | 0.10% | 0.11% |

It will be noted that each final fraction B5', B5", B5'" comprises isoprene in a mass fraction of less than 15% and that the mass ratio (methyl butenes:isoprene) within the final fractions B5' and B5" is approximately 60% and 50%, respectively.

Furthermore, as mentioned in § III. 2) b) above, the hydrogenation stage, by the insufficient reduction in the amount of n-pentenes which it produces, does not make it possible to obtain a ratio (1,3-pentadiene:isoprene) in the final fractions B5', B5" and B5'" which is at most equal to 0.5%.

d) Dehydrogenation of the Intermediate Fraction B6 in Order to Obtain Three Final Fractions B6', B6' and B6'", Whether or Not in Accordance with the Invention Table 9 below shows the compositions of final fractions according to the invention B6', B6", B6'" respectively obtained by dehydrogenation operations applied to the intermediate fraction B6 in accordance with § III. 2) a) above, at temperatures of 600, 625 and 650° C.

TABLE 9

|  | Initial fraction B | Intermediate fraction B6 | Final fraction B6': dehydrogen. at 600° C. | Final fraction B6": dehydrogen. at 625° C. | Final fraction B6''': dehydrogen. at 650° C. |
|---|---|---|---|---|---|
| isoprene |  | not determined | 9.70% | 10.10% | 10.30% |
| 1-pentene | 4.20% | ≈59 ppm | 143 ppm | 133 ppm | 154 ppm |
| 2-pentene (E + Z) | 15.10% | ≈9 ppm | 335 ppm | 358 ppm | 398 ppm |
| 1,4-pentadiene:isoprene |  |  | 0.02% | 0.03% | 0.03% |
| 1,3-pentadiene:isoprene |  |  | 0.50% | 0.60% | 0.70% |
| 2-methyl 1-butene | 11.20% | 0.70% | 2.50% | 2.20% | 1.80% |
| 3-methyl 1-butene | 1.60% | 38 ppm | 0.50% | 0.50% | 0.30% |
| 2-methyl 2-butene | 16.70% | 17.70% | 4.30% | 3.70% | 2.90% |
| isopentane | 41.10% | 51.60% | 50.10% | 49.50% | 48.90% |
| Pentane | 4.60% | 24.70% | 25.50% | 25.30% | 25.60% |
| Total methyl butenes | 29.50% | 18.40% | 7.30% | 6.40% | 5.00% |
| Total n-pentenes | 19.30% | ≈68 ppm | 478 ppm | 491 ppm | 552 ppm |
| Total α-olefins | 17.00% | 0.70% | 3.00% | 2.70% | 2.10% |
| Total β-olefins | 31.80% | 17.70% | 4.30% | 3.70% | 2.90% |
| Total mono-olefins | 48.80% | 18.40% | 7.30% | 6.40% | 5.00% |

It will be noted that each final fraction B6', B6" and B6''' is characterized in that it comprises isoprene in a mass fraction practically equal to or less than 10%.

It will also be noted that the final fractions B6', B6" comprise methyl butenes in a mass ratio (methyl butenes:isoprene) practically equal to or greater than 50%.

But it will be noted that only the final fraction B6' (characterized by a dehydrogenation temperature of 600° C.) is usable to polymerize isoprene selectively with satisfactory conversion kinetics close to those relating to the isolated polymerization of isoprene and in order to obtain a polyisoprene of high viscosity analogous to that of polyisoprene obtained in isolation, owing to the fact that only this fraction B6' according to the invention is characterized by a ratio (1,3-pentadiene:isoprene) of less than or equal to 0.5%.

IV. Comparative Example, not in Accordance with the Invention, of a C' fraction Enriched with Isoprene by Dehydrogenation, from a Fluid Catalytically Cracked Initial Fraction C, without Hydrogenation of this Initial Fraction C:

Catalytic dehydrogenation of an initial C5 fraction C was carried out directly in the manner described in § III. 2) a) above, to obtain a final C5 fraction C enriched with isoprene.

Table 10 hereafter shows the respective compositions of these fractions C and C'.

TABLE 10

|  | Initial C5 fraction C | Dehydrogenated C5 fraction C' |
|---|---|---|
| Isoprene | 0.41% | 15.05% |
| Isopentane | 42.98% | 40.61% |
| 2-pentene (E + Z) | 14.38% | 2.80% |
| 1-pentene | 4.86% | 0.85% |
| 2-methyl 1-butene | 11.51% | 3.39% |
| 3-methyl 1-butene | 2.47% | 0.78% |
| 2-methyl 2-butene | 14.41% | 5.24% |
| 1,4-pentadiene | 0.02% | 0.21% |
| 1,3-pentadiene (E + Z) | 0.39% | 4.6% |
| Cyclopentadiene | 0.21% | 0.31% |
| Total methyl butenes | 28.39% | 9.41% |
| Total n-pentenes | 19.24% | 3.65% |

It will be noted that the absence of prior hydrogenation of the initial fraction C before the dehydrogenation stage results in an excessively high mass fraction of 1,3-pentadiene being obtained in the dehydrogenated fraction C' (4.6% instead of the upper limit permissible according to the invention of 0.5%), which does not make it possible to selectively polymerize isoprene from this fraction and by means of the catalytic system of § I. with satisfactory conversion kinetics which are close to those relating to the isolated polymerization of isoprene (i.e. the polymerization medium comprising solely the cyclohexane solvent and the isoprene), nor to obtain a polyisoprene of high viscosity which is analogous to that of polyisoprene obtained in isolation.

APPENDIX 1

Determination of the Microstructure of the Polyisoprenes

By the Technique of Carbon-13 Nuclear Magnetic Resonance ($^{13}C$ NMR analysis):

a) Preparation of the Samples:

2 g of polyisoprene are extracted in refluxing acetone for 8 hours. The extracted polyisoprene is then dried at ambient temperature under vacuum for 24 hours. This dried polyisoprene is then redissolved in chloroform. The polyisoprene solution is filtered and the solvent removed in a rotary evaporator for 4 hours (bath temperature is 40° C.).

For the purposes of the analysis, approximately 600 mg of the polyisoprene thus prepared is solubilised in $CDCl_3$ (2 ml), directly in a $^{13}C$ NMR tube.

b) Characteristics of the Apparatus:

Spectrophotometer sold under the name "BRUKER AM250".

Resonance frequency (SFO)=62.9 MHz.

Pulse program: INVGATE.AU (suppression of the "NOE" effect for quantitative NMR analysis of $^{13}C$).

Pulse duration: 9 µs (90°).

Relaxation time: 10 s.

Cumulative number of scans (NS)=8192.

c) Assignment of the Peaks of the Spectrum:

Peaks were identified after:

Quang Tho Pham, R. Petiaud, H. Waton, M. F. Llauro Darricades, "*Proton and NMR Spectra of Polymers*", 1991, Penton Press.

d) Integration Method:

No 1,2 structural units detected.

The ratio between 3,4- and 1,4-contents is determined by means of the ethylenic carbons. The content of trans-1,4 and cis-1,4 linkages in the polyisoprene is calculated from the aliphatic carbons.

APPENDIX 2

Determination of the Distribution of the Molecular Weights of the Elastomers Obtained by Size Exclusion Chromatography (SEC)

a) Principle of the Measurement:

Size exclusion chromatography or SEC makes it possible physically to separate macromolecules according to their size in the swollen state in columns filled with porous stationary phase. The macromolecules are separated by their hydrodynamic volume, the bulkiest being eluted first.

Although not an absolute method, SEC does enable an assessment to be made of the molecular weight distribution of a polymer. On the basis of commercially available standards, the various number-average (Mn) and weight-average (Mw) molecular weights can be determined and the polydispersity index calculated (Ip=Mw/Mn).

b) Preparation of the Polymer:

There is no particular treatment of the sample of polymer before analysis. It is simply solubilised in tetrahydrofuran, at a concentration of approx. 1 g/l.

c) SEC Analysis:

The apparatus used is a "WATERS model 150C" chromatograph. The elution solvent is tetrahydrofuran, the flow rate is 0.7 ml/min, the temperature of the system is 35° C. and the duration of analysis is 90 min. A set of four columns in series is used, of the trade names "SHODEX KS807", "WATERS type STYRAGEL HMW7" and two "WATERS STYRAGEL HMW6E".

The volume of polymer sample solution injected is 100 μl. The detector is a "WATERS model RI32X" differential refractometer and the chromatographic data processing software is the "WATERS MILLENNIUM" system (version 3.00).

APPENDIX 3

Determination of the Compositions of the C5 Fractions by Gas Phase Chromatography (GPC)

a) GPC/FID Analysis:

Analysis of each C5 fraction is effected from the injected volume of 0.2 μl without prior dilution, in order not to saturate the response of the flame ionisation detector (FID) used.

b) Chromatographic conditions used:

Chromatograph HP6890

Carrier gas: nitrogen

Constant flow rate: 0.7 m/min.

Method of injection: "split"

Ratio of "split": 50/1

Temperature of the injector: 250° C.

Injected volume: 0.2 μl

Column HP 1:
  phase 100% of methyl polysiloxane
  length: 60 m
  internal diameter: 0.32 mm
  thickness of the film: 1 μm Temperature program: T1=15° C.
  D1=20 min.
  P1=20° C./min.
  T2=280° C.
  D2=4 min.

FID temperature: 300° C.

Results;

Semi-quantitative analysis was performed by calculating the relative proportion of the areas of the peaks of each chromatogram, in order to obtain a distribution. The differences in responses of the eluted compounds were not taken into consideration, as the FID did not detect signals due to the presence of non-eluted and eluted compounds. The proportion in % of a compound i is given by the following expression:

$$\% \ i = A_i / \Sigma A_i \times 100$$

where $A_i$=area relative to the compound i, and
$\Sigma A_i$=total of all the eluted compounds i (identified and non-identified).

The invention claimed is:

1. A process for obtaining, from a fluid catalytically cracked initial C5 fraction, a final C5 fraction which is enriched with isoprene and purified and usable to form a medium for the selective polymerization of isoprene in the presence of a catalytic system based on a conjugated diene, a rare earth salt of an organic phosphoric acid suspended in a saturated inert hydrocarbon solvent, an alkylaluminum of formula $AlR_3$ or $HAlR_2$ in which Al represents an aluminium atom, H represents a hydrogen atom and the radicals R, which may be identical or different, and straight-chain or branched, represent hydrocarbon groups having from 1 to 8 carbon atoms, and an alkylaluminum halide, said process comprising:

a catalytic hydrogenation reaction of said initial C5 fraction by means of a palladium-based catalyst, which produces an intermediate C5 fraction comprising n-pentenes in a mass ratio which is less than 0.1%, and methyl butenes, a dehydrogenation reaction which is applied to the intermediate C5 fraction, comprising methyl butenes, and which produces said final C5 fraction, and purification of said final C5 fraction thus obtained to obtain said purified final C5 fraction which is essentially free of disubstituted alkynes, true alkynes and cyclopentadiene.

2. The process according to claim 1, wherein a mass fraction of said methyl butenes in said intermediate C5 fraction is less than or equal to 20%.

3. The process according to claim 1, wherein said purified final C5 fraction comprises isoprene in a mass fraction of less than 30%.

4. The process according to claim 3, wherein said purified final C5 fraction comprises isoprene in a mass fraction of less than or equal to 10%.

5. The process according to claim 1, wherein said purified final C5 fraction comprises 1,3-pentadiene and 1,4-pentadiene in mass ratios (1,3-pentadiene:isoprene) and (1,4-pentadiene:isoprene) which are less than or equal to 0.5% and 0.2% respectively.

6. The process according to claim 1, wherein a mass ratio (methyl butenes:isoprene) is equal to or greater than 50% in said purified final C5 fraction.

7. A process for obtaining an isoprene homopolymer having a cis-1,4 linkage content equal to or greater than 98.0%, which comprises the reaction, in a polymerization medium comprising isoprene and at least one methyl butene, wherein the mass ratio (methyl butene(s):isoprene) is greater than 50%, and the mass ratio of isoprene in the polymerization medium is less than 30%, of a catalytic system comprising:
- at least one conjugated diene monomer,
  - a salt of one or more rare earth metals of an organic phosphoric acid, said salt being suspended in at least one saturated inert aliphatic or alicyclic hydrocarbon solvent,
  - an alkylaluminum of the formula $AlR_3$ or $HAlR_2$, in which Al represents an aluminium atom, H represents a hydrogen atom and the radicals R, which may be identical or different, and straight-chain or branched, represent hydrocarbon groups having from 1 to 8 carbon atoms, the molar ratio (alkylating agent:rare earth salt) ranging from 1 to 5, and
  - a halogen donor comprising an alkylaluminum halide.

8. The process according to claim 7, wherein said polymerization medium includes at least one mono-olefin, wherein a mass ratio (mono-olefin(s):isoprene) is greater than 50%.

9. The process according to claim 7 wherein said methyl butene(s) comprise(s) 2-methyl 2-butene.

10. The process according to claim 9, wherein said methyl butenes comprise 2-methyl 1-butene and 2-methyl 2-butene, the mass ratio (2-methyl 1-butene:isoprene) and the mass ratio (2-methyl 2-butene:isoprene) each being between 20% and 60%.

11. The process according to claims 7, 8, 9 or 10, wherein the mass fraction of isoprene in said polymerization medium is less than or equal to 10%.

12. The process according to claim 7 which comprises the following steps:
(i) catalytically hydrogenating by means of a palladium-based catalyst, a fluid catalytically cracked initial C5 fraction to provide an intermediate C5 fraction comprising methyl butenes in a mass fraction of less than 30%,
(ii) obtaining, by dehydrogenation of said intermediate C5 fraction, a final C5 fraction which is enriched with isoprene,
(iii) effecting a purification of said final C5 fraction which is essentially free of disubstituted alkynes, true alkynes and cyclopentadiene, and
(iv) reacting said purified final C5 fraction with said catalytic system.

13. The process according to claim 12, wherein the mass fraction of said methyl butenes in said intermediate C5 fraction is less than or equal to 20%.

14. The process according to claim 12, wherein said purified final C5 fraction comprises isoprene in a mass fraction of less than or equal to 10%.

15. The process according to claim 12, wherein said intermediate C5 fraction comprises said n-pentenes in a mass fraction of less than 0.1%.

16. The process according to claims 12, 13, 14 or 15, wherein said purified final C5 fraction comprises 1,3-pentadiene and 1,4-pentadiene in mass ratios (1,3-pentadiene:isoprene) and (1,4-pentadiene isoprene) which are respectively less than or equal to 0.5% and to 0.2%.

17. The process according claim 12, wherein a mass ratio (mono-olefines:isoprene) is equal to or greater than 50% in said purified final C5 fraction.

18. The process according to claim 12, which further comprises a stage of purification of said final C5 fraction, to obtain said purified final C5 fraction comprising disubstituted alkynes, in a mass ratio (disubstituted alkynes:isoprene) in said purified C5 fraction of less than or equal to 0.7%.

19. The process according to claim 7, wherein the polymerization of isoprene is effected at a temperature less than or equal to 5° C., and said isoprene homopolymer has a cis-1,4 linkage content, measured according to the techniques of carbon 13 nuclear magnetic resonance or of mid-infrared analysis, which varies from 99.0% to 99.6%.

20. The process according to claim 7, wherein said isoprene homopolymer has an inherent viscosity, measured at 0.1 g/dl in toluene at 25° C., which is greater than 4 dl/g.

21. The process according to claim 7, wherein said rare earth salt is a tris[bis(2-ethylhexyl)phosphate]of rare earth(s).

22. The process according to claim 12, wherein said catalytic system satisfies at least one of the following conditions:
(a) said rare earth metal(s) are present in a concentration within a range of from 0.01 to 0.06 mol/l,
(b) the molar ratio (halogen donor:rare earth salt) varies from 2.0 to 3.5,
(c) the molar ratio (conjugated diene monomer:rare earth salt) varies from 15 to 70,
(d) said conjugated diene monomer is butadiene,
(e) said alkyl aluminium is diisobutylaluminum hydride, and
(f) said halogen donor is diethylaluminium chloride.

23. The process according to claim 21, wherein the rare earth is neodymium.

* * * * *